United States Patent
Shimizu et al.

(10) Patent No.: US 7,488,825 B2
(45) Date of Patent: Feb. 10, 2009

(54) METHOD FOR PREPARING POLYMORPHISM OF IRINOTECAN HYDROCHLORIDE

(75) Inventors: Hideaki Shimizu, Tokyo (JP); Atsuhiro Abe, Tokyo (JP); Takashi Yaegashi, Tokyo (JP); Seigo Sawada, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 10/546,687

(22) PCT Filed: Feb. 24, 2004

(86) PCT No.: PCT/JP2004/002126
§ 371 (c)(1),
(2), (4) Date: Jun. 19, 2006

(87) PCT Pub. No.: WO2004/076460
PCT Pub. Date: Sep. 10, 2004

(65) Prior Publication Data
US 2006/0234904 A1 Oct. 19, 2006

(30) Foreign Application Priority Data
Feb. 25, 2003 (JP) ............................. 2003-046908

(51) Int. Cl.
*C07D 491/22* (2006.01)
(52) U.S. Cl. .......................................... 546/48; 546/42
(58) Field of Classification Search .................. 546/48, 546/42
See application file for complete search history.

(56) References Cited

FOREIGN PATENT DOCUMENTS

| | | |
|---|---|---|
| JP | 62-47193 | 10/1987 |
| JP | 3-4077 | 1/1991 |
| JP | 7-277981 | 10/1995 |
| JP | 10-017472 | 1/1998 |
| JP | 2005-525367 | 8/2005 |
| WO | 03/074527 | 9/2003 |

OTHER PUBLICATIONS

Pages 12, 14, 18 and 19 of 60/360,684.*
Seigo Sawada: Synthesis and Antitumor Activity of 20(S)-Camptothecin Derivatives: Carbamate-Linked, Water-Soluble Derivatives of 7-Ethyl-10-hydroxycamptothecin1), Chemical & Pharmaceutical Bulletin, vol. 39, No. 6, pp. 1446-1454, 1991.

* cited by examiner

*Primary Examiner*—Charanjit S Aulakh
(74) *Attorney, Agent, or Firm*—Oblon, Spivak, McClelland, Maier & Neustadt, P.C.

(57) ABSTRACT

A method for preparing a novel crystalline polymorphic irinotecan hydrochloride which is excellent in the solubility in water and reduced in the content of impurities is provided. A method for preparing c-type crystals of irinotecan hydrochloride having diffraction peaks (2θ) at 9.15°, 10.00°, 11.80°, 12.20°, 13.00° and 13.40° in the powder X-ray diffractometry characterized by mixing irinotecan with one or more solvents selected from the group consisting of acetone, acetonitrile and tetrahydrofuran, adding hydrochloric acid, and collecting the formed crystals.

3 Claims, 4 Drawing Sheets

(i) c-type crystals (Example 1, No.3)

(ii) b-type crystals (Comparative product)

METHOD FOR PREPARING POLYMORPHISM OF IRINOTECAN HYDROCHLORIDE

TECHNICAL FIELD

The present invention relates to a method for preparing c-type crystals of irinotecan hydrochloride excellent in the solubility in water and reduced in the content of impurities.

BACKGROUND ART

Camptothecin (CPT) is an alkaloid contained in the leaf or bark of *Camptotheca acumination* originated from China. CPT is a substance having excellent antitumor property; however, hardly soluble in water. Therefore, a semi-synthetic derivative of CPT, namely, irinotecan hydrochloride (7-ethyl-10-[4-(l-piperidino)-1-piperidino]carbonyloxycam ptothecin hydrochloride (hereinafter sometimes referred to as "CPT-11") has been developed as a medicament (Japanese Patent Publication No. 3-4077). Irinotecan hydrochloride retaining high antitumor properties of CPT and mitigated in toxicity, has been widely used as an antitumor agent. When metabolized within the body, irinotecan hydrochloride is said to convert into 7-ethyl-10-hydroxycamptothecin (SN-38) (Japanese Patent Publication No. 62-47193), thereby giving rise to antitumor activity.

Irinotecan hydrochloride is administered to a patient primarily by intravenous injection. At present, therefore, irinotecan hydrochloride is sold and used in the form of an isotonic preparation treated with sorbitol or saline. Up to now, various attempts have been made to produce a preparation. For example, JP-A-1995-277981 reports a sustained release preparation, which is formed by adding a camptothecin derivative in a copolymer of collagen and 2-hydroxyethyl methacrylate. JP-A-1998-17472 reports a sustained release preparation formed by adding camptothecin or its derivative to a carrier formed of a polylactic acid-glycolic acid copolymer.

DISCLOSURE OF THE INVENTION

Conventionally, amorphous irinotecan hydrochloride and crystalline irinotecan hydrochloride (b-type crystals) have been used. However, the amorphous irinotecan hydrochloride has a problem in that the water content varies depending upon humidity change during formation of a preparation, varying dissolution conditions. On the other hand, the crystalline irinotecan hydrochloride is present in the form of trihydrates; however, it is hardly solved in water without raising temperature. In the circumstances, it has been desired to develop a method for preparing a novel crystalline polymorphic irinotecan hydrochloride which is excellent in water solubility and reduced in the content of impurities.

Accordingly, an object of the present invention is to provide a method for preparing a novel crystalline polymorphic irinotecan hydrochloride which is excellent in the solubility in water and is reduced in the content of impurities.

The present inventors paid attention to crystalline polymorphism, a phenomenon where substances having the same chemical structure show different physical properties such as different melting points and solubilities. As a result of intensive studies, they found that a novel crystalline polymorphic (c-type crystals) irinotecan hydrochloride more excellent in water solubility than conventional irinotecan hydrochloride crystallized from water, and low in impurity content, can be obtained by mixing irinotecan with a predetermined solvent, adding hydrochloric acid to the mixture and crystallizing irinotecan hydrochloride. Based on the finding, the present invention was accomplished.

To be more specifically, a method for preparing c-type crystals of irinotecan hydrochloride having diffraction peaks (2θ) at 9.15°, 10.00°, 11.80°, 12.20°, 13.00° and 13.40° in the powder X-ray diffractometry characterized by mixing irinotecan with one or more solvents selected from the group consisting of acetone, acetonitrile and tetrahydrofuran, adding hydrochloric acid, and collecting the formed crystals.

The preparation method of the present invention is easily performed. The c-type crystalline irinotecan hydrochloride prepared by the invention is excellent in water solubility, extremely reduced in the content of impurities such as decomposed matter and prepared without subjecting to a temperature raising operation, and thus extremely useful as a basic ingredient of an irinotecan hydrochloride preparation.

BEST MODE OF CARRYING OUT THE INVENTION

Figure 1:
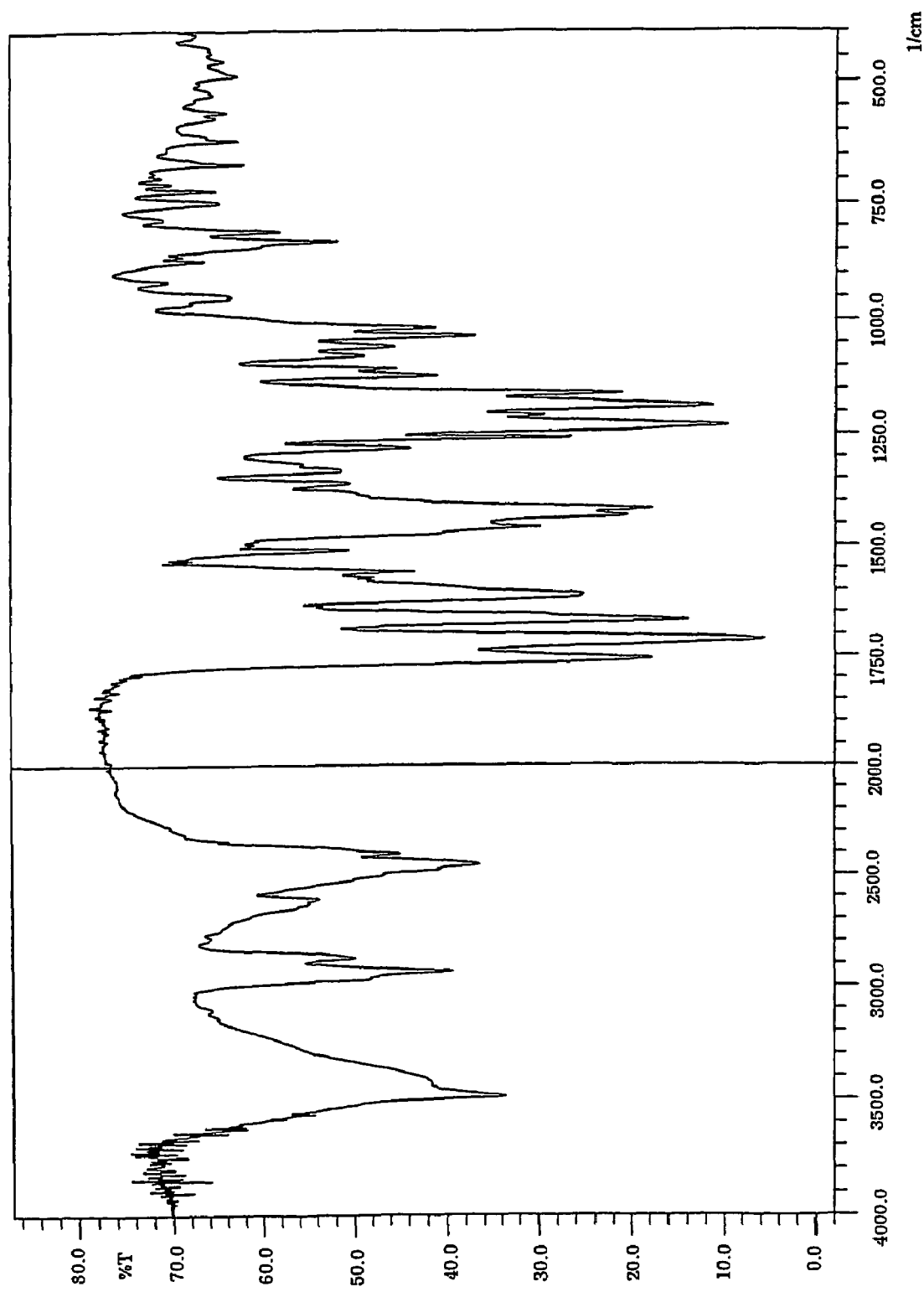
FIG. 1 is a graph showing an infrared absorption spectrum of the irinotecan hydrochloride crystals obtained.

Irinotecan (7-ethyl-10-[4-(1-piperidino)-1-piperidino]carbonyloxycam ptothecin) to be used in the present invention can be prepared by a method disclosed in Japanese Patent Publication No. 3-4077.

As the solvent to be mixed with irinotecan, use may be made of a solvent mixture of one or two types or more selected from the group consisting of acetone, acetonitrile and tetrahydrofuran. Furthermore, the solvent to be used in the present invention is preferably present in the anhydrous form.

The mixing ratio (by weight) of irinotecan to a solvent is not particularly limited; however, in view of the yield of c-type crystals, the mixing ratio of a solvent relative to irinotecan being one part is preferably 30 to 1000 parts by weight, 50 to 600 parts by weight, particularly 70 to 500 parts by weight.

In mixing irinotecan with a solvent, it is preferable to add an auxiliary agent for filtration such as medicinal carbon, activated carbon, Celite, or silica gel. This is because impurities are easily removed from the raw material during filtration.

To the mixture of irinotecan and a solvent, hydrochloric acid is added to produce irinotecan hydrochloride. In this way, irinotecan is dissolved in the solvent. In theory, the addition amount of hydrochloric acid should be an equivalent mole relative to irinotecan; however, in view of the yield of c-type crystals, 1.0 to 2.0 times by mole, 1.0 to 1.8 times by mole, particularly 1.0 to 1.5 times by mole is preferable. The addition temperature is not particularly limited; however, a temperature of 5 to 30° C., in particular, 12 to 25° C. is preferable.

After hydrochloric acid is added, c-type crystals may be added as a seed crystals in order to facilitate crystallization of the c-type crystals of irinotecan hydrochloride. The crystallization conditions are not particularly limited; however, it is preferable that the mixture is stirred at 5 to 30° C., further at 10 to 25° C. for 2 to 200 hours, and further for 10 to 120 hours.

The c-type crystals of irinotecan hydrochloride thus formed can be collected by means of filtration or centrifugation.

The c-type crystals of irinotecan hydrochloride thus collected may be subjected to a moisture absorption process performed by a customary method using a saturated aqueous sodium chloride solution or a saturated aqueous ammonium nitrate solution.

The irinotecan hydrochloride thus obtained is c-type crystals, which is more excellent in water solubility than the b-type crystals crystallized from a supersaturated aqueous solution of irinotecan hydrochloride. To describe more specifically, the water solubility of the b-type crystals at pH3.5 is 11.4 mg/mL, whereas that of the c-type crystals is 100 mg/mL or more.

The c-type crystals has diffraction peaks ($2\theta$) at 9.15°, 10.00°, 11.80°, 12.80°, 13.00° and 13.40°, whereas the b-type crystals has diffraction peaks ($2\theta$) at 7.60°, 8.30°, 9.55°, 11.00° and 12.40°, in the powder X-ray diffractometry. Form this, it is clear that the c-type crystals differs from the b-type crystals and therefore, the c-type crystals is a novel crystals polymorphism. Furthermore, the c-type crystals has an infrared absorption spectrum ($v$) having peaks at 1757, 1712 and 1667 $cm^{-1}$. In this respect, the c-type crystals differs from the b-type crystals having peaks at 1748, 1688 and 1663 $cm^{-1}$. Also, the c-type crystals is irinotecan hydrochloride sesquihydrates. Note that a peak ($2\theta$) obtained in the powder X-diffractometry has an error of ±0.2, whereas the infrared absorption spectrum has an error of about ±5 $cm^{-1}$.

The c-type crystals of irinotecan hydrochloride formed by the preparation method of the present invention can be used as an antitumor agent in the same manner as in b-type crystals of irinotecan hydrochloride formed by a conventional method and administered by various methods including injections such as intravenous injection, subcutaneous injection, and intramuscular injection, and oral administration. In particular, intravenous administration (injection) and oral administration are preferable.

In the case of intravenous administration, the dose varies depending upon the therapeutic purpose; however, a dose of 5 to 400 mg/adult per day, in particular, 20 to 200 mg/adult per day, is preferable. In the case of oral administration, a dose of 50 to 2,000 mg/adult, in particular, 100 to 1,000 mg/adult per day, is preferable.

In the case of oral administration, a preparation is preferably formed such that it can be suitably absorbed from the gastrointestinal tract. Examples of such a form include tablets, powders, capsules, or soft capsules, and peroral liquid preparations such as an aqueous suspension solution, solution, and syrup. In the case of injection, an ample of a predetermined dose is preferable. To such a preparation, a preservative or the like may be used.

EXAMPLES

The present invention will be described in more detail below by way of examples, which should not be construed as limiting the present invention.

Example 1

Irinotecan was suspended in acetonitrile or acetone in accordance with the amounts shown in Table 1 and dissolved by adding, 6 mol/L hydrochloric acid. To each mixture solution, 1 mg of c-type crystals separately prepared was added and the solution was stirred at 22° C. for 25 to 46 hours. The formed crystals were obtained by filtration, dried under reduced pressure, and subjected to a moisture absorption process performed by a saturated aqueous sodium chloride solution method until the crystals showed constant weight (about 80 hours). In this manner, the crystals of irinotecan hydrochloride were obtained.

Table 1 shows the results of the preparations.

TABLE 1

| No. | Irinotecan (g) | Solvent[1] Acetonitrile | Acetone | Hydrochloric acid[2] | Seed crystals | Crystallization time (hour) | Yield (%) |
|---|---|---|---|---|---|---|---|
| 1 | 5.0 | 80 | | 1.0 | — | 46 | 83.4 |
| 2 | 5.0 | 120 | | 1.0 | c form | 25 | 80.5 |
| 3 | 10.0 | 120 | | 1.05 | c form | 41 | 76.3 |
| 4 | 1.0 | | 360 | 1.05 | c form | 41 | 91.7 |

[1]mL/g (Irinotecan)
[2]Times by mole relative to irinotecan

The crystals of irinotecan hydrochloride obtained above were subjected to infrared absorption spectrum analysis, powder X-ray diffraction analysis, and thermoanalysis. The results are shown in FIGS. 1 to 3.

In the infrared absorption spectrum, strong absorption was observed at wavelengths of about 1757 $cm^{-1}$, 1712 $cm^{-1}$, 1667 $cm^{-1}$ (FIG. 1).

Figure 2:
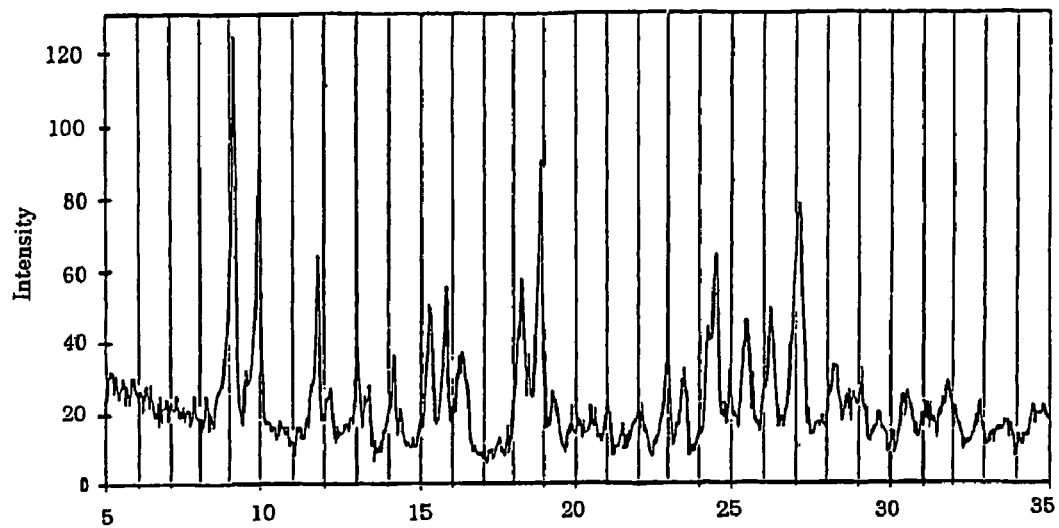
FIG. 2 is a graph showing the powder X-ray diffractometry of the irinotecan hydrochloride crystals obtained.

In the powder X-ray diffraction, diffraction peaks ($2\theta$) were observed at 9.15°, 10.00°, 11.80°, 12.20°, 13.00° and 13.40°; however no strong peak was observed at 11.00°, which is intrinsic to the b-type crystals (FIG. 2).

Figure 3:
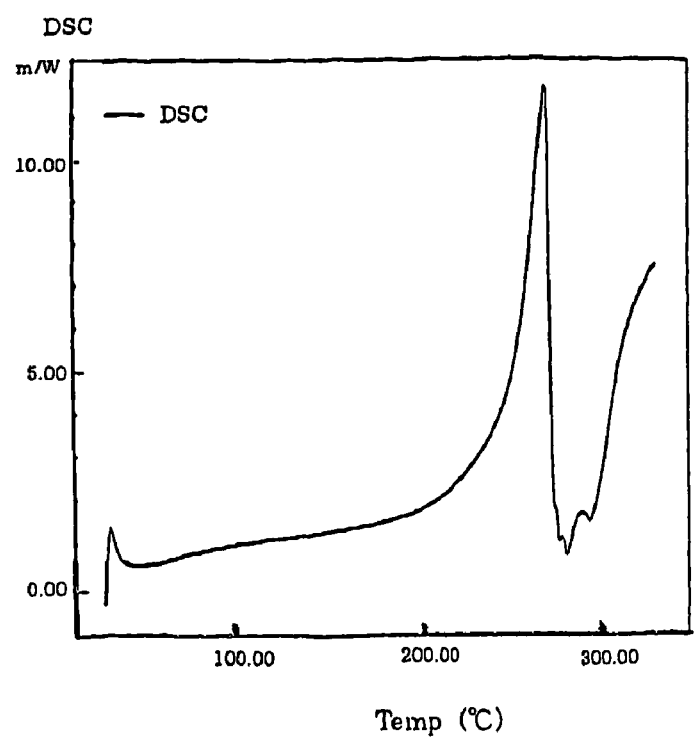
FIG. 3 is a graph showing the results of thermoanalysis (differential scanning calorimetry) for the irinotecan hydrochloride crystals obtained.

In the thermoanalysis (differential scanning calorimetry), an endothermic peak near 90° C. due to dehydration was not observed, which is intrinsically observed in the b-type crystals (FIG. 3).

The moisture content of the crystals was measured by the Karl Fischer method. As a result, the moisture content of No. 3 was 3.96%. Therefore, it turned out that the crystals above were obtained in the form of sesquihydrates (calculation value: 4.15%).

From the results above, it was confirmed that the crystals of irinotecan hydrochloride prepared in accordance with Nos. 1 to 4 are c-type, which are different from the b-type crystals conventionally crystallized from water.

Example 2

The irinotecan hydrochloride prepared in Example 1 was measured for water solubility and stability over time.

Note that irinotecan hydrochloride b-type crystals was formed as a comparative product in accordance with the following method.

Formation of a Comparative Product (b-Type Crystals)

Ten grams of irinotecan was suspended in about 100 mL of purified water. About 10 mL of diluted hydrochloric acid (the Japanese Pharmacopoeia) was added dropwise to the suspension solution while stirring. Then, irinotecan was dissolved by raising temperature of the suspension solution. After the resultant solution was filtered, a seed crystals was added to the filtrate, which was stirred at room temperature for about 50 hours to form crystals. The resultant crystals were subjected to suction filtration and a filtrated product was dried under reduced pressure. A dried product was allowed to stand still in a humidifier to humidify in accordance with a saturated aqueous sodium chloride solution method.

Solubility Measurement

About 0.5 g of b- or c-type crystals were weighed out, suspended in a preparation solution, and shaken at 22° C. for 30 minutes (130 r/min). The mixture was filtered by a membrane filter (0.45 μm). To 1 ml of the filtrate, the preparation solution was added up to 200 mL. 10 μl was aliquoted and analyzed by liquid chromatography. The dissolution amount was obtained on the basis of a calibration curve previously prepared.

Note that the preparation solution used herein was prepared by dissolving 45 g of D-sorbitol in an appropriate amount of distilled water for injection, adding 900 mg of lactic acid, adjusting pH of the solution at about 3.5, and adding distilled water for injection up to 1000 mL.

The c-type crystals of No. 3 according to the present invention was dissolved upon adding the preparation solution and provided a dissolution amount of 100 mg/mL or more, meaning that they are extremely easily dissolved in water, whereas, the b-type crystals (a comparative product) exhibited a dissolution amount of 11.4 mg/mL. Accordingly, it was demonstrated that the c-type crystals prepared by the method according to the present invention is extremely excellent in water solubility compared to the b-type crystals.

Change of dissolution state over time

The b- or c-type crystals was dissolved in a preparation solution to a concentration of 30 mg/mL and filtered by a membrane filter (0.22 μm). The filtrate was aliquoted and allowed to stand still at 22° C. in the dark.

The c-type crystals (No. 3) prepared by the method of the present invention was dissolved at room temperature by shaking for 1 to 2 minutes, whereas, the b-type crystals was not dissolved until the solution was heated to about 70° C. and shaken for several minutes. The filtrates of c-type and b-type crystals were both stable in 3 months or more. Neither color-tone change (yellowing change) nor precipitation was observed.

Stability Test Over Time

The c-type crystals (Example 1, No. 3) was placed in lightproof airtight containers (screw-top brown vial shielded by a Parafilm) and stored in a laboratory (about 15° C.) and a refrigerator (about 5 to 10° C.) and thereafter subjected to infrared absorption spectrum analysis, thermoanalysis, and Karl Fischer analysis for measuring a moisture content. As a result, no change was observed in comparison with the state before storage.

Example 3

Figure 4:
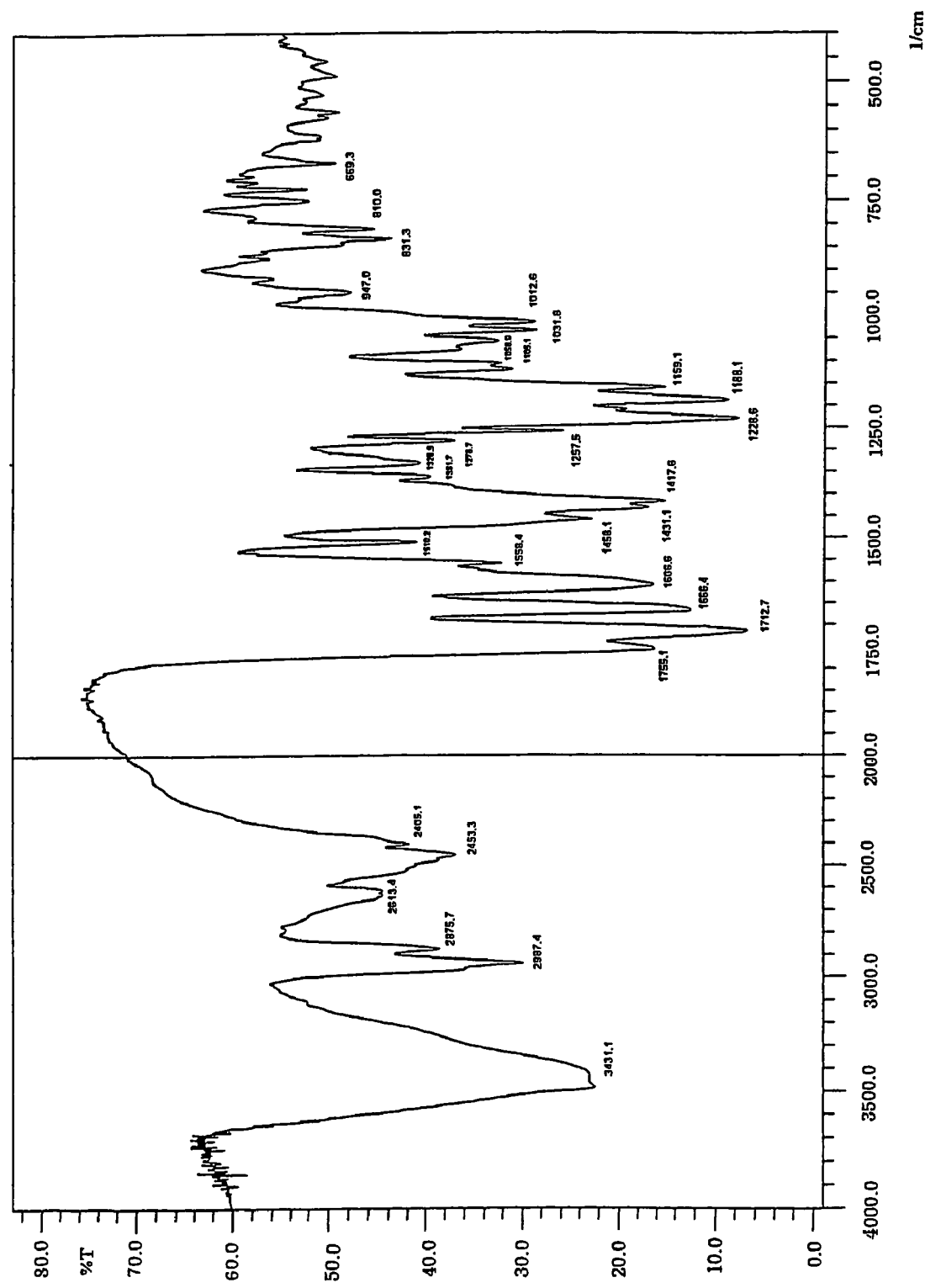
FIG. 4 is a graph showing the infrared absorption spectrum of a preparation formed by using medicinal carbon according to Example 3.
Figure 5:
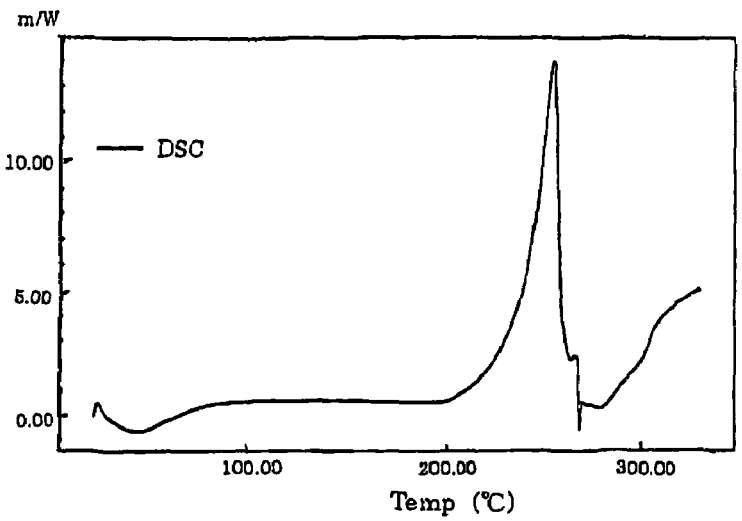
FIG. 5 is a graph showing the results of thermoanalysis (differential scanning calorimetry) of a preparation formed by using medicinal carbon according to Example 3.

One gram of irinotecan was added to 120 mL of tetrahydrofuran. The resultant solution was stirred for 30 minutes in the presence or absence of 0.2 g of medicinal carbon. The medicinal carbon was filtered off by a membrane filter. While stirring the filtrate, 6 mol/L hydrochloric acid was added in an amount 1.05 times by mole as large as irinotecan and subjected to the same process as in Example 1. Note that the moisture absorbing time until the solution reached constant weight was about 100 hours. The results of infrared absorption spectrum and thermoanalysis (differential scanning calorimetry) for crystals obtained in a system having medicinal carbon added thereto are shown in FIGS. 4 and 5. It was confirmed that the obtained crystals is c-type crystals.

The yield of the c-type crystals was 85.6% in the case where medicinal carbon was added and 100% in the case where no medicinal carbon was added.

Example 4

Purity Test

The c-type crystals prepared by the method of the present invention and the b-type crystals prepared as a comparative product in Example 2 were subjected to a purity test in accordance with the following method.

Purity test: To 0.05 g of the c-type or b-type crystals, a solution mixture containing 0.01 mol/L potassium dihydrogen phosphate, methanol and acetonitrile in a ratio of 6:4:3 was added to prepare a sample solution of 20 mL. A 1-ml aliquot was accurately taken from the sample solution. To the aliquot, the solution mixture containing 0.01 mol/L potassium dihydrogen phosphate, methanol and acetonitrile in a ratio of 6:4:3 was added to prepare a standard solution of exactly 100 mL. An aliquot of 20 μL was taken from each of the sample solution and the standard solution and subjected to HPLC to determine the contents of analogous substances in the following operation conditions.

The total content of analogous substances (%)=(the peak areas of substances except for irinotecan hydrochloride in the sample solution)/(the peak area of irinotecan hydrochloride in the standard solution)

The content of each analogous substance (%)=(the peak area of each analogous substance in the sample solution)/(the peak area of irinotecan hydrochloride in the standard solution).

Operation Conditions for HPLC

Mobile phase: Solution mixture of 0.01 mol/L potassium dihydrogen phosphate/methanol/acetonitrile (6:4:3) containing 0.005 mol/L sodium 1-decane sulfonate.

Detection: an ultraviolet absorptiometer (measurement wavelength: 254 nm)

Column: InertsilODS-2 (5 μm; 4.6 mmID×25 cm)

Column temperature: a constant temperature of about 40° C.

Flow rate: about 1 mL/min

Figure 6:
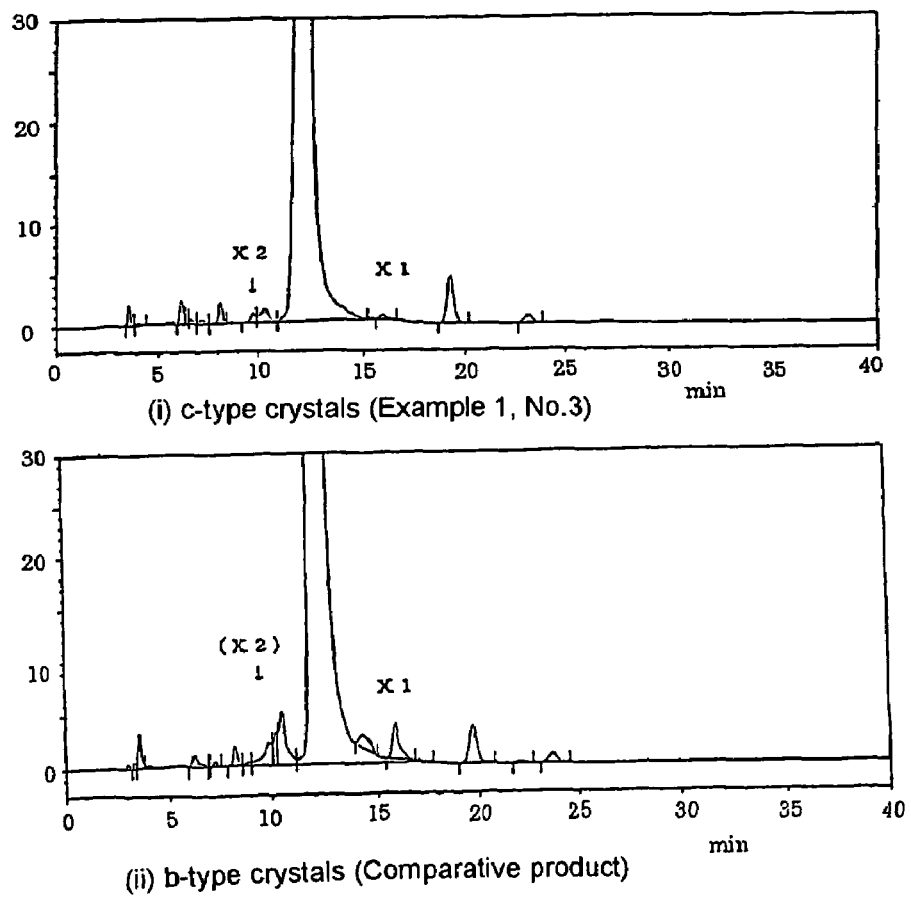
FIG. 6 is a HPLC chart of a purity test.

The results of the purity test are shown in FIG. 6 and Table 2.

Based on the HPLC retaining time, analogous substances contained in irinotecan hydrochloride were determined as follows. A substance showing retention time (RT) of 6.4 minutes was determined as 7-ethyl-10-hydroxycamptothecin, a substance of 10.1 minutes as a decomposed product (X2) and a substance of 16.1 minutes as a decomposed product (X1).

The b-type crystals of irinotecan hydrochloride (comparative product) contained decomposed products (X1 and X2) in an amount of 0.17% by weight, whereas, the c-type crystals of irinotecan hydrochloride prepared by the method of the present invention had the decomposed products in an amount as low as 0.03 to 0.04% by weight, suggesting that the purity of the c-type crystals according to the present invention is high.

TABLE 2

| | (weight %) | | |
| --- | --- | --- | --- |
| | c-type crystals | | |
| Retaining time (minute) | Example 1 No. 3 | Example 3 using carbon | b-type crystals |
| 6.4 | 0.03 | 0.01 | 0.01 |
| 10.0 | 0.03 | 0.03 | 0.12 |
| 16.1 | <0.005 | 0.01 | 0.05 |
| (Analogous substances)[3] | 0.23 | 0.22 | 0.36 |

[3] Total content of analogous substances each having different retention time

The invention claimed is:

1. A method for preparing c-type crystals of irinotecan hydrochloride, comprising:

mixing irinotecan with one or more solvents selected from the group consisting of acetone, acetonitrile and tetrahydrofuran;

adding hydrochloric acid to the mixture to form crystals; and collecting the formed crystals;

wherein the crystals have diffraction peaks (2θ) at 9.15°, 10.00°, 11.80°, 12.20°, 13.00° and 13.40° in powder X-ray diffractometry.

2. The method for preparing c-type crystals of irinotecan hydrochloride according to claim 1, wherein the crystals have an infrared absorption spectrum having peaks at 1757, 1712 and 1667 cm$^{-1}$.

3. The method for preparing c-type crystals of irinotecan hydrochloride according to claim 1 or 2, wherein the crystals are present in the form of sesquihydrates.

* * * * *